US009730923B2

(12) United States Patent
Lagarde et al.

(10) Patent No.: US 9,730,923 B2
(45) Date of Patent: *Aug. 15, 2017

(54) ANTIPROLACTINIC VETERINARY COMPOSITION FOR RUMINANTS

(75) Inventors: Anouck Lagarde, Floirac (FR); Stephane Floch, Galgon (FR); Thierry Bertaim, Coutras (FR)

(73) Assignee: Ceva Sante Animale, Libourne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/081,671

(22) Filed: Apr. 7, 2011

(65) Prior Publication Data

US 2011/0245261 A1 Oct. 6, 2011

Related U.S. Application Data

(63) Continuation-in-part of application No. PCT/EP2009/063004, filed on Oct. 7, 2009.

(30) Foreign Application Priority Data

Oct. 7, 2008 (FR) ...................................... 08 05544

(51) Int. Cl.

| A61K 31/48 | (2006.01) |
|---|---|
| A61K 31/381 | (2006.01) |
| A61K 31/4035 | (2006.01) |
| A61K 31/428 | (2006.01) |
| A61K 31/47 | (2006.01) |
| A61K 31/473 | (2006.01) |

(52) U.S. Cl.

CPC ............ *A61K 31/48* (2013.01); *A61K 31/381* (2013.01); *A61K 31/4035* (2013.01); *A61K 31/428* (2013.01); *A61K 31/47* (2013.01); *A61K 31/473* (2013.01)

(58) Field of Classification Search

CPC ..................................................... A61K 31/48
See application file for complete search history.

(56) References Cited

FOREIGN PATENT DOCUMENTS

| EP | 1952813 A | 8/2008 |
|---|---|---|
| WO | WO 00/54776 A | 9/2000 |
| WO | WO 03/043653 A | 5/2003 |
| WO | 2004113378 | 12/2004 |
| WO | WO 2004/113375 | 12/2004 |
| WO | WO 2004/113378 A2 * | 12/2004 |

(Continued)

OTHER PUBLICATIONS

Bradley AJ and Green MJ, A Study of the Incidence and Significance of Intramammary Enterobacterial Infections Acquired During the Dry Period. J Dairy Sci; 2000, 83:1957-1965.*

(Continued)

*Primary Examiner* — Marcos Sznaidman
*Assistant Examiner* — Rayna B Rodriguez
(74) *Attorney, Agent, or Firm* — Leason Ellis LLP

(57) ABSTRACT

This present invention relates to an antiprolactinic veterinary composition to be administered to ruminants. Said composition comprises at least one antiprolactinic compound which is an agonist of dopamine receptors, and is particularly useful for promoting a substantial reduction of lactation, mammary involution, and for treating and/or intramammary diseases or infections of ruminants.

4 Claims, 2 Drawing Sheets

(56) References Cited

FOREIGN PATENT DOCUMENTS

WO 2009003965 1/2009
WO WO2009/003965 A1 * 1/2009

OTHER PUBLICATIONS

LeBlanc SJ, Lissemore KD, Kelton DF, Duffield TF, and Leslie KE. Major Advances in Disease Prevention in Dairy Cattle. J. Dairy Sci.; 2006, 89:1267-1279.*
Zhao X and Lacasse P. Mammary tissue damage during bovine mastitis: Causes and control. J. Anim. Sci.; 2008, 86(Suppl. 1):57-65, originally published online Sep. 4, 2007.*
Prevent—Cambridge Dictionary Online.*
Stein et al ("Mammary Gland Involution as a Multi-step Process." J Mammary Gland Biol Neoplasia. 2007; 12:25-35).*
Robert et al ("Pregnancy outcome after treatment with the ergot derivative, cabergoline." Reproductive Toxicology, 1996; 10(4):333-337).*
Blackwell et al (Endocrinology of Breast Cancer, Contemporary Endocrinology vol. 11, 1999, p. 3-20).*
Ricci et al (Reproductive Toxicology, 2002; 16:791-793).*
Hearn et al (Journal of Reproduction and Fertility, 1998; 113:151-157).*
PCT International Search Report, Nov. 24, 2009, for Ceva Sante Animale Sa et al., Int'l App'l No. PCT/EP2009/063004, filed Oct. 7, 2009.
PCT Written Opinion of the International Searching Authority, Nov. 24, 2009, for Ceva Sante Animale Sa et al., Int'l App'l No. PCT/EP2009/063004, filed Oct. 7, 2009.
Akers et al., 1981, "Prolactin Regulation of Cytological Differentiation of Mammary Epithelial Cells in Periparturient Cows", Endocrinology, vol. 109(1): 31-40. (Abstract only).
Buys et al., 1995, "Bromocriptine is Effective in Reducing Milk Production in Ewes during Lactation, But Has No Additional Effect During Drying Off", Animal Science (Pencaitland), vol. 60(2): 203-208.
Forsyth et al., 1993, "Bromocriptine Treatment of Periparturient Goats: Long-Term Suppression of Prolactin and Lack of Effect of Lactation", Journal of Dairy Research, vol. 60(3): 307-317.
Forsyth et al., 1935, "Hormone Concentrations Marnmmary Development and Milk Yield in Goats Given Long-Term Bromocriptine treatment in Pregnanacy", Journal of Endocrinology, vol. 104(1): 77-83. (Abstract only).
Leitner et al., 2007. "Casein Hydrolyzate Intrammammary Treatment Improves the Comfort Behavior of Cows Induced into Dry-Off", Livestock Science, vol. 110(3):292-297.
Peterson et al., 1997, "Long-Term Bromocriptine Treatment during Late Pregnancy Has Differential Effects on Milk Yields of Single- and Twin-bearing Ewes", New Zealand Journal of Agricultural Research, vol. 40(2): 249-259.
Brooks DJ, 2000, "Dopamine agonists: their role in the treatment of Parkinson's disease", Journal Neurol Neurosurg Psychiatry, vol. 68: 685-689.
Katznelson et al., 2011, "Prolactin and its Disorders", Endocrinology, Chapter 13, http://medtextfree.wordpress.com/2011/12/19/chapter-13-prolactin-and-its-disorders/.
Bradley AJ and Green MJ, 2000, "A Study of the Incidence and Significance of Intramammary Enterobacterial Infections Acquired During the Dry Period", Journal Dairy Sci, vol. 83: 1957-1965.
Leblanc et al., 2006, "Major Advances in Disease Prevention in Dairy Cattle", Journal Dairy Sci, vol. 89: 1267-1279.
Zhao X and Lacasse P, 2008, "Mammary tissue damage during bovine mastitis: Causes and Control", Journal Anim Sci, vol. 86(Suppl. 1): 57-65, originally published online Sep. 4, 2007.

* cited by examiner

ANTIPROLACTINIC VETERINARY COMPOSITION FOR RUMINANTS

This application is a Continuation-in-part of Int'l App'l No. PCT/EP2009/063004, filed Oct. 7, 2009, which claims priority of French Application No. 0805544, filed Oct. 7, 2008. The entire contents and disclosures of the preceding applications are incorporated by reference into this application.

This invention concerns an antiprolactinic veterinary composition to be administered to ruminants. This composition consists of at least one antiprolactin agonist of dopamine receptors and is particularly useful in favoring mammary involution, the regeneration of the mammary tissue and the conditions of the reduction of the lactation. Besides, the compositions according to this invention can be administered during periods of gestation as they do not present any deleterious or abortive effects on the gestation of ruminants.

In ruminants, lactation in general lasts between 5 to 20 months, and lasts approximately about 10 months in dairy cows. After this lactation period, the milking is generally stopped suddenly and the cow is put to rest during a period of time that traditionally lasts about 60 days (known as dry period) up to the calving, which is the starting point of the subsequent lactation. In dairy farming, this drying period is known to substantially improve the health and welfare of the ruminants. This kind of physiological rest provided to the udder is necessary for the regeneration of the mammary glands and preparation of subsequent lactations. It also limits the emergence of health-related troubles caused during the milking and calving, such as the emergence of intra-mammary inflammations and intra-mammary infections that have a significant economic impact.

Antiprolactinic compounds are prescribed in medicines for humans to treat hyperprolactinemia, pituitary adenomas, Parkinson disease or even to provoke the stopping of lactation in certain women who cannot breast-feed due to medical reasons. Such medicines contain inhibitors of prolactin hypophyseal as the active principal, a hormone that activates milk secretion. It concerns medicines such as PARLODEL® (bromocriptine, Novartis), DOSTINEX® OR CABASER® (cabergoline, Pfizer) for which usage is explicitly prohibited during pregnancy because of their deleterious effects on the fetus. At the moment of the prescription for stopping the milking, it is recommended to administer them right after the delivery in order to stop the rise of the milk within twenty-four hours.

In veterinary medicine, compositions are based of prolactin inhibitors such as GALASTOP® (Cabergoline, Ceva Sante animale) can be further administered as treatments for lactations of pseudo gestations in female cats and dogs. They are also prescribed following early weaning or abortions or during the immediate withdrawal after birth or parturition. In animals, as in human patients, prolactin secreting inhibitors have always been prescribed after gestation or pregnancy because of the toxicity, risks of malformed fetus and the risks of spontaneous abortions.

In ruminant mammals, it has been established that prolactin plays an important role for the maturing of the mammary glands and the start up of the lactation after weaning, but does not affect the production of milk during the established lactation (Karg H. & Shams D., J. Reprod Fertil., 1974 August; 39(2); 463-72—Shams et al., Experentia, 1972; (28): 697-699—Akers et al., Endocrinology, 1981; (109): 23-30—Plant K. et al., Domest Anim Endocrinol, 1987; (4); 279-290—Knight, Livestock Production Science, 2001, (70); 87-93—Dalh et al, J; Anim. Sci., 2003; (81), supl3; 11-17).

Contrary to many publications indicating that the diminishing of the prolactin has very weak or no effect on the production of milk during the lactation established in principal dairy animals, such as cows and goat, the applicant surprisingly discovered that a single dose of an antiprolactinic compound agonist of dopamine receptors led to a substantial reduction of lactation and allowed the efficient induction of the initial phase of drying up which consists of mammary involution.

Similarly and against all expectations, the applicant found out that the veterinary compositions comprising antiprolactinic compounds that are agonists of dopamine receptors can be administered to ruminants in order to induce a reduction of lactation, promote mammary involution and the conditions of drying of the tissue and this, during gestation without creating any deleterious or abortive effects.

The administration of these veterinary compositions to ruminants has revealed itself to be particularly advantageous as it allows a significant reduction of lactation and promotes mammary involution and this even during the gestation period, resulting in an improvement of drying conditions. Besides, veterinary compositions ensure a significant improvement of the health of the udder, a better regeneration of damaged secretary tissues of the udder, as well as a reduction of the frequency of intra-mammary diseases and/or infections and for example the mastitis of the ruminants during the subsequent lactations.

SUMMARY OF THE INVENTION

This invention relates to veterinary compositions comprising at least one antiprolactinic compound agonist of dopamine receptors to be administered to ruminants. The antiprolactin compounds of veterinary compositions according to the invention are chosen among the ergoline-derived dopamine receptor agonists or non ergoline-derived dopamine receptor agonist.

According to the invention, these compositions are administered in therapeutically effective amounts, particularly as single treatment, in order to induce a reduction of lactation. Also, these compositions can also be administered to gestating ruminants without causing any deleterious or abortive effects on the gestation. They provide a significant welfare of the ruminants, and are particularly useful in mammary involution in ruminants, in the treatment and/or the prevention of intra-mammary inflammations and intra-mammary infections of ruminants. The present invention further relates to methods of inducing mammary involution in ruminants, as well as methods of prevention and/or treatment of intra-mammary infections of ruminants, such as for example mastitis. The present invention finally relates to kits for promoting mammary involution, and reduction of milk production in the ruminants, as well as kits for the treatment and/or the prevention of mastitis in the said ruminants.

DETAILED DESCRIPTION OF THE INVENTION

Figure 1:
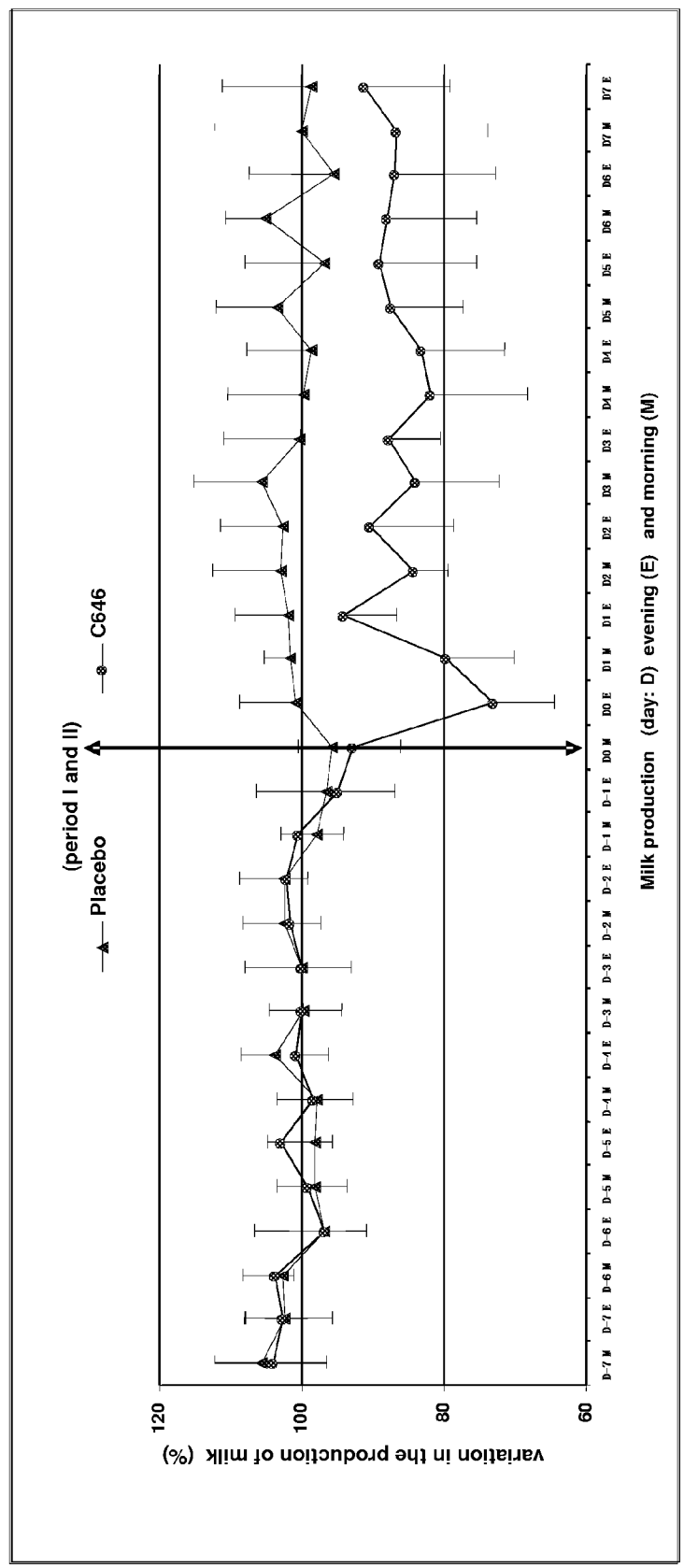
FIG. 1: is a graph showing the variation of the percentage of the milk production in the morning and in the evening day D-7 and day D7 (in comparison to a baseline of 100) following a single injection of 5 mcg/kg of cabergoline on day D0, in a group of placebo and in a group of treated animals (C646)

This invention relates to a veterinary composition consisting of at least one antiprolactinic compound agonist of dopamine receptors administered in a single dose in order to induce the reduction of the lactation in the treated animal as of the first milking after treatment and next milking. This invention relates to the usage of the said veterinary composition administered in sufficient therapeutic quantities in one single dose, to induce a substantial reduction of the lactation.

Prolactin is a hypophyseal hormone that has mammotropic and lactogenic effects, which means that it activates the growth of mammary glands and milk secretion. The release of prolactin is stimulated by the prolactoliberine and inhibited by the dopamine. The inhibiting action of the dopamine on the pituitary gland is mediated by the post-synaptic receptors of dopamine, such as in particular D2 receptor.

The compounds are known as antiprolactinic when they inhibit the release of prolactin. It may concern dopaminergic compounds or serotoninergic compounds. The dopaminergic compounds are agonist of dopamine receptors which bind to dopamine receptors present in particular on prolactin secretory cells on the adenohypophysis in order to inhibit the prolactin secretion.

Preferably, these antiprolactinic dopaminergic compounds bind to dopamine receptors. Most preferably, these compounds specifically bind to the D2 dopamine receptors. These antiprolactinic antiserotoninergic compounds act by stimulating dopamine release in the hypothalamus, resulting in the inhibition of prolactin secretion. The veterinary compositions according to the present invention preferably comprise antiprolactinic dopaminergic compounds.

These antiprolactinic compounds may be chosen among ergoline-derived dopamine receptor agonists and/or derivatives thereof. These ergoline derivatives are well known in the public domain and have the following general structure:

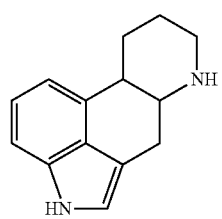 [SMILES: c1cc2c3c(c[nH]c3c1)CC1NCCCC21]

Examples of ergoline-derived antiprolactinic agonists are cabergoline, metergoline, lisuride, bromocriptine, ergometrine, as well as all the derivatives of the compounds sharing an antiprolactinic activity.

Cabergoline whose chemical name is N-[3-(Dimethylamino)propyl]-N-[(ethylamino)carbonyl]-6-(2-propenyl)-8g-ergoline-8-carboxamide, is a antiprolactinic agonist specific of D2 dopamine receptors. In particular, it is described in the U.S. Pat. No. 4,526,892. Its developed chemical formula is as follows:

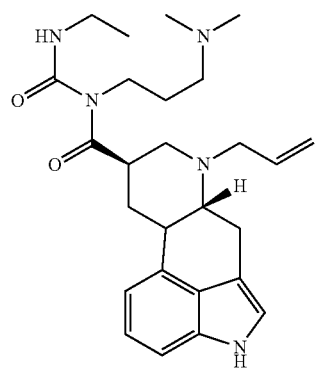 [SMILES: C=CCN1C[C@H](C(=O)N(CCCN(C)C)C(=O)NCC)CC2c3cccc4[nH]cc(c34)C[C@H]21]

Cabergoline constitutes the active principle of drugs for humans marketed under denominations such as DOSTINEX® AND/OR CABASER® (cabergoline, Pfizer). Also, this is the basic active principle for veterinary compositions marketed under the denomination GALASTOP® (Cabergoline, Ceva Sante animale) intended for female dogs prone to lactations during pseudo-gestation. Whether it is DOSTINEX® (Cabergoline, Pfizer) or GALASTOP® (Cabergoline, Ceva Sante animale), these compositions made up of a cabergoline base are never administered during pregnancy or gestation.

Metergoline is a synthetic compound known under the chemical name of benzyl I ((6aR,9S,10aR)-4,7-dimethyl-4,6,6a,7,8,9,10,10a-octahydroindolo-[4,3-fg]quinolin-9-yl) methyl carbamate. This is an antiprolactinic compound that binds to dopamine receptors, as well as to serotonin receptor 5HT, and therefore activates the release of dopamine and the inhibition of the prolactin secretion. Metergoline has the following chemical structure:

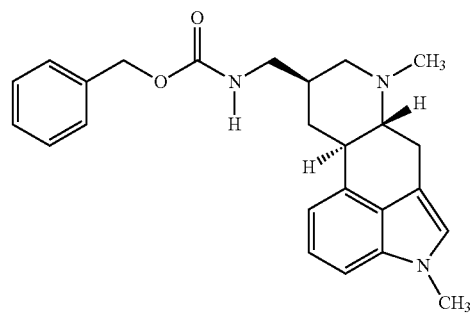 [SMILES: CN1C[C@H](CNC(=O)OCc2ccccc2)C[C@@H]2c3cccc4c3c(cn4C)C[C@H]21]

Lisuride, also known by its chemical name 1,1-diethyl-3-((6aR,9S)-7-methyl-4,6,6a,7,8,9-hexahydroindolo[4,3-fg]quinolin-9-yl) urea present in the developed chemical formula is as follows:

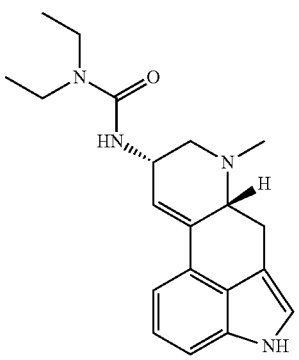 [SMILES: CCN(CC)C(=O)N[C@H]1C=C2c3cccc4[nH]cc(c34)C[C@H]2N(C)C1]

This is an agonist compound that is a dopaminergic inhibitor of prolactin. It is marketed under the name of AROLAC® (Liruside, Lisapharm Laboratoire) for the treatment of amenorrhea and hyperprolactemenia in human patients.

Bromocriptine is known under the name of bromo-2 ergocryptine and under the chemical name ergotaman-3', 6', 18-trione, 2-bromo-12'-hydroxy-2'-(1-methylethyl)-5' alpha-(2-methylpropyl). Its chemical formula is as follows:

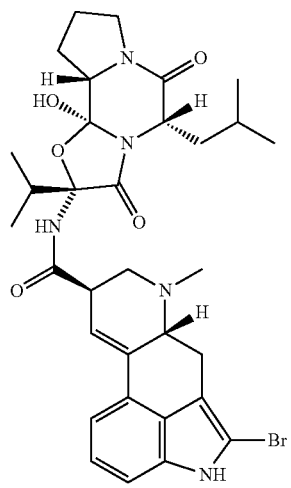

Compositions such as PARLODEL® (Bromocriptine, Novartis) and BROMO-KIN® (Bromocriptine, Sanofi Aventis) used in particular for the treatment of tumors of the pituitary gland and hyperprolactinemias, or in gynecology for inhibiting lactation after delivery, comprise of a therapeutically effective amount of bromocriptin which is an ergoline-derived dopaminergic agonists.

Ergometrine or ergonovine, denonimated further as d-lysergic beta-propanolamide can also be incorporated into veterinary compositions as antiprolactinic dopaminergic agonist. Its chemical formula is as follows:

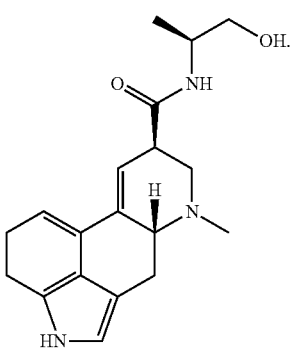

Other antiprolactinic compounds that are agonist of dopamine receptors can be used in compositions of the present invention and can be administered to ruminants, particularly during the gestation period. These can be chosen from antiprolactinic compounds that are non-ergoline-derived dopamine receptor agonists. Examples of such compounds are ropinirol, pramipexole, rotigotine, and quinagolide, as well as derivatives thereof having antiprolactinic activity.

Ropinirol whose chemical name is 4-(2-dipropylamino-ethyl)-1,3-dihydroindol-2-one, acts as an agonist of dopamine receptors D2 and D3. Its chemical formula is as follows:

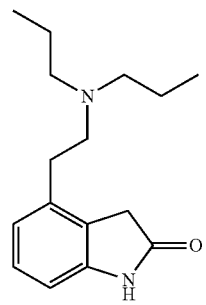 [SMILES: CCCN(CCC)CCc1cccc2c1CC(=O)N2]

Ropinirol is found in compositions of products such as REQUIP® (Ropinirole GlaxoSmithKline) and ROPARK® (Ropinirole, Sun) prescribed in medicines for humans for the treatment of Parkinson's disease.

Pramipexole represents another dopaminergic agonist which binds in particular to the receptors D2 and D3 of dopamine. Its chemical name is (6S)—$N^6$-propyl-4,5,6,7-tetrahydro-1,3-benzothiazole-2,6-diamine and its formula is as follows:

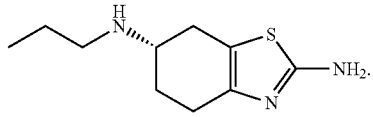

Pramipexole is well known in the pharmaceutical field since it is marketed under the names MIRAPEX® (pramipexole dihydrochloride, Boehringer Ingelheim International GmbH), MIRAPEXIN® (pramipexole dihydrochloride monohydrate, Boehringer Ingelheim International GmbH) and SIFROL® (pramipexole dihydrochloride monohydrate, Boehringer Ingelheim International GmbH) for the treatment of Parkinson's disease and the syndrome of restless legs.

Rotigotine which is equally known under the chemical denomination of 6-(propyl-(2-thiophen-2-ylethyl)amino)tetralin-1-ol. Its chemical formula is as follows:

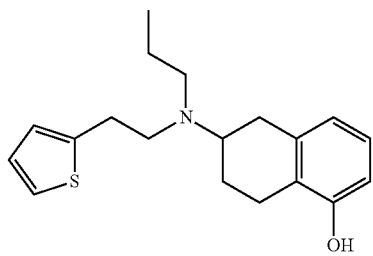 [SMILES: CCCN(CCc1cccs1)C1CCc2c(O)cccc2C1]

Rotigotine was recently approved for the treatment of Parkinson's disease by transdermal administration in the form of a patch under the designated name of NEUPRO® (Rotigotine, UCB).

Quinagolide or (3R,4aR,10aS)-3-(diethylsulfamoylamino)-6-hydroxy-1-propyl-3,4,4a,5,10,10a-hexahydro-2H-benzo[g]quinoline is an inhibitor of prolactin secretion as well. This is a specific agonist of D2 dopamine receptors. Its chemical formula is as follows:

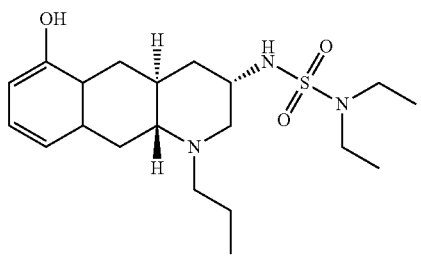 [SMILES: CCCN1C[C@@H](NS(=O)(=O)N(CC)CC)C[C@@H]2CC3C(O)=CC=CC3C[C@H]21]

Quinagolide is marketed under the commercial name of NORPROLAC® (Quinagolide, Ferring Pharmaceuticals) for the treatment of macroprolactinoma or hyperprolactinemia.

These series of compounds have always been administered up to now, outside of pregnancy or gestation.

The applicant however surprisingly discovered that these compounds, when administered to ruminants, in a therapeutically effective amount and in a single administration, in fact induced a significant reduction of the lactation, promoting mammary involution and improving the reduction of lactation. Contrary to what was known until now, these compounds were revealed by the applicant to be particularly beneficial as they allow effective reduction of milk production, particularly during the gestation period of ruminants without provoking any deleterious or abortive effects. Finally, the compositions according to this invention ensured a significant decrease in the risks of mastitis in the treated ruminants.

As demonstrated in the Examples below, one single dose can be administered to non-human animals in order to promote mammary involution and reduction of the lactation, whether in periods of gestation or after calving. The amounts or therapeutically effective doses may vary depending on the ruminants to be treated and the mode of administration of the compositions. These doses can be easily determined by systematic trials based on the below Examples that can be readily used by skilled persons in the art. Examples of therapeutically effective doses according to the present invention comprise between 5 and 50 mcg/kg, or between 5 and 25 mcg/kg.

Preferably, according to the present invention, the compositions are administered in single doses per treatment and animal so as to obtain a substantial reduction of lactation comprising between 5 and 60%, between 20 and 50%, or even between 25 and 35%, over a period from 1 day, 2 days, 3 days, 4 days, 5 days or 6 days, and up to 7 days after the administration of the composition. As demonstrated in Example 2, the reduction of the lactation is significant as of the first milking, but even during the following milking.

It is possible to administer compositions according to the present invention to the ruminants in gestation and more precisely during the latter two thirds of the gestation, without causing any abortive or deleterious effects. As examples, the veterinary compositions can be administered from the 3$^{rd}$ month or more during the period of gestation of dairy cows. They are preferably be administered to gestating ruminants between the 3$^{rd}$ and the 8$^{th}$ months of gestation.

According to the present invention, ruminants are intended to mean herbivorous mammals such as bovines, ovines, goats, or camelids. The compositions of the present invention are administered to milk-producing mammary ruminants such as preferably dairy cows and sheeps.

According to the present invention, the compositions can be administered during the gestation period or outside of the gestation period. They promote the reduction of the lactation and act on successive hormonal, physiological or morphological changes that affect the udders during the drying period, and particularly from the initial phase of the drying up, mammary involution during which the secretory tissue is disrupted and atrophied. Surprisingly, no deleterious or toxic effect, malformation of the fetus or even any abortive effect was reported when they were administered during the gestation period of the ruminants.

Veterinary compositions according to the present invention can be administered according to many ways of administration that are well known in the field and adapted to the treatment of each of these animals. They are preferably administered cutaneously, orally or parenterally. It is even more preferential to administer them parenterally, and particularly through intramuscular or subcutaneous injection. They are in appropriate forms for the selected mode of administration. They can therefore be in the form of a solution or an oral or injectable suspension liquid, or in a solid or semi-solid form, in powder form, capsule, granule, sugar, coated tablet, soft capsule, sprays, caplet, pills, tablets, or pastes.

Advantageously, the veterinary composition is administered in one single injectable dose.

Depending on the formulations and drugs, the veterinary compositions may further comprise pharmaceutical conventional ingredients for the preparation of liquid or solid formulations to be administered orally or parenterally. Moreover, in the case of oral formulations, these can be administered directly to the ruminants or can be mixed into the food.

Furthermore, the compositions according to the invention may comprise depending on the type of formulation, a solvent, a flowing agent, a lubricant and any suitable mass excipient such as lactose, cellulose or starch. As lubricant, one can use stearic acid, magnesium stearate, L-leucine or for example, glyceryl tribehenate. As a disintegrating agent, one can use sodium carboxymethyl starch, or reticulated sodium carboxymethyl starch. As a flowing agent, one can use pure silicon or silicon dioxide colloidal. Oral solid forms can be in the form of tablets covered with coating.

The injectable preparations are prepared by mixing effective therapeutic quantities of at least one anti prolactinic compound as described previously with a solvent, a pH regulator, a buffer agent, a suspending agent, a solubilization agent, a stabilizer, an agent of tonicity and/or a preservative, and by transforming the mix with a traditional process for cutaneous or intramuscular injection. Examples of solvents are oily solvents such as medium chain triglycerides in $C_8$-$C_{10}$, or a mix of capric acid, caprylic acid, and triglycerides, such as those marketed under the name of MYGLIOL® 812 (Caprylic/Capric Triglyceride). Injectable preparations can be freeze-dried according to a traditional process.

Examples of suspending agents include methylcellulose, polysorbate 80, hydroxyethyl cellulose, xanthan gum, sodium carboxymethyl cellulose, sorbitane monolaureate polyethylene. Examples of solubilization agents include ricin oil solidified by polyoxyethylene, polysorbate 80, nicotinamide, sorbitane monolaureate polyethoxylated, macrogol and ester ethyl fatty ricin acid. Besides, the stabilizing agent includes sodium sulfate, sodium metasulfate and ester, while the preservative includes methyl p-hydroxybenzoate, ethyl p-hydroxybenzoate, sorbic acid, benzyl alcohol, phenol, cresol and chlorocresol. One example of the agent of tonicity is mannitol. During the preparation of solutions and injectable suspensions, it is better to ensure that they are isotonic with blood.

Advantageously, the veterinary compositions of the present invention can be administered in association with standard treatments of mastitis of ruminants. Examples of standard care or prophylactic compositions of mastitis are local disinfectants for udders, antibiotics such as penicillins of group M, cephalosporine, gentamycin or colistine or even enzymes such as lysozymes or muramidase.

This present invention further relates to the use therapeutically effective amount of at least one antiprolactinic compound acting as an agonist of dopamine receptors as described previously for the preparation of veterinary compositions to be administered to ruminants during or outside of gestation period for improving their well being and their health, for promoting the reduction of the milk production, for promoting mammary involution, and for treating and/or preventing intra-mammary inflammations and intra-mammary infections. When these veterinary compositions are administered during the gestation period in therapeutic doses that are suitable for the maintenance of gestation, they do not cause any deleterious or abortive effects.

This invention further relates to methods of reducing milk production as well as to methods for the treatment and/or the prevention of mastitis comprising administering the veterinary compositions as previously described in therapeutically effective amount by cutaneous, oral or parenteral administration to the ruminants. The methods according to this invention are particularly advantageous as they promote mammary involution and the reduction of the lactation of the ruminants, even during gestation without causing any deleterious and abortive effects.

This present invention in addition relates a veterinary kit useful to promote the reduction of milk production of the ruminants, to improve the welfare and health of the ruminants, as well as promote mammary involution, treat and/or prevent intra-mammary diseases and/or infections and particularly of mastitis. The kits according to this invention consists of at least one compartment for an eventually sterile conditioning comprising a therapeutically effective amount of at least one antiprolactinic compound agonist of dopamine receptors as described previously for administration to ruminants. The kit comprises means of administering the compositions cutaneously, orally or by parenterally as well as an instruction sheet concerning the mode of administration of the veterinary compositions of the present invention.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended and does not exclude additional, un-recited elements or method steps.

EXAMPLES

Example 1: Preparation of Veterinary Compositions with a Cabergoline Base

Preparation of 9 liters of an injectable solution containing 500 mcg/ml of cabergoline.
Formula:
    Active principle: 4.53 g of cabergoline (titrating 100%)
    Excipient: triglycerides of a medium chain q. s. 9 I.
Step 1: 4.53 g of cabergoline and 1.5 kg medium chain triglycerides were measured in a recipient of adequate capacity, and then a mix was shaken with a magnetic shaker (500 turns per minute) for at least 60 minutes for complete dissolving.
Step 2: In a dry recipient, 5 kg medium chain triglycerides were measured, the flow of nitrogen and the mixer were set and then the cabergoline in a concentrated solution, obtained at step 1, was added to the recipient. The shaking was maintained for 30 minutes and then the volume was brought to a final volume of 9 liters by adding medium chain triglycerides. The shaking was still maintained for another 30 minutes and then solution was filtered under pressurized nitrogen through a calibrated cartridge of 0.45 microns. The filtrate was collected in an appropriate flask previously disinfected by vapor and dried with a flow of nitrogen. The solution obtained was sterilized at 121° C. during 15 minutes, and then was put into sterilized, non-pyrogenic flasks shut with rubber stoppers and aluminum capsules, washed and passed through the autoclave.

Example 2: Clinical Study of the Efficiency of the Cabergoline Based Veterinary Compositions in Ruminants This study aimed to evaluate the reduction of milk production in 8 multipare cows of the Prim Holstein family in lactation for 6 months. These cows were aged between 3 and 9 years and have a level of production varying between 20 and 31 kg per day at the start of this study. The study was organized according to a design of cross-over (2 treatments×2 periods).

The formulation was described in Example 1, containing 500 mcg/ml of cabergoline in injectable solution that was used in this study.

Treatment Test (C646): Injectable solution of cabergoline of 500 mcg/ml, 1 single intramuscular injection of a dose of 5 mcg/kg that is 1 ml for 100 kg of body weight.

Treatment Control (Placebo): water for the preparation of injectable, 1 intramuscular injection of a volume identical to that of the treatment test of about 1 ml for 100 kg.

The sequence of the treatment was randomized (A-B or B-A) with a wash-out period of 3 weeks between 2 treatments. The individual milk production was observed at each milking during a period of 7 days prior to the treatment and 7 days after the treatment. Blood samples were taken daily in order to monitor the evolution of prolactin plasmatic concentrations, during a period lasting from 2 days before the treatment to 7 days after the treatment.

The results shown in FIG. 1, show that the injection of the treatment Test of a dose of 5 mcg/kg caused a reduction in milk production:
    From the 1$^{st}$ milking following the injection of the treatment Test (12 h), the reduction of the milk production was approximately of a 27%, and could go up to 42% according to the individuals/subjects.

During the follow up period of the 7 days after the treatment Test, the total reduction of the milk production was approximately 15%, and could go up to 27% according to individuals/subjects.

While generalizing the results on a population of cows, these results provided an estimate a reduction of the milk production from the 1$^{st}$ milking between 5 and 60% depending on the animals. The reduction in milk production after the injection of the treatment Test is presumably between 25 and 35% as the following milking. This decrease was maintained during for approximately 2 days. A progressive resumption of the milk production was then observed, nonetheless however without regaining its initial level after a week.

Figure 2:
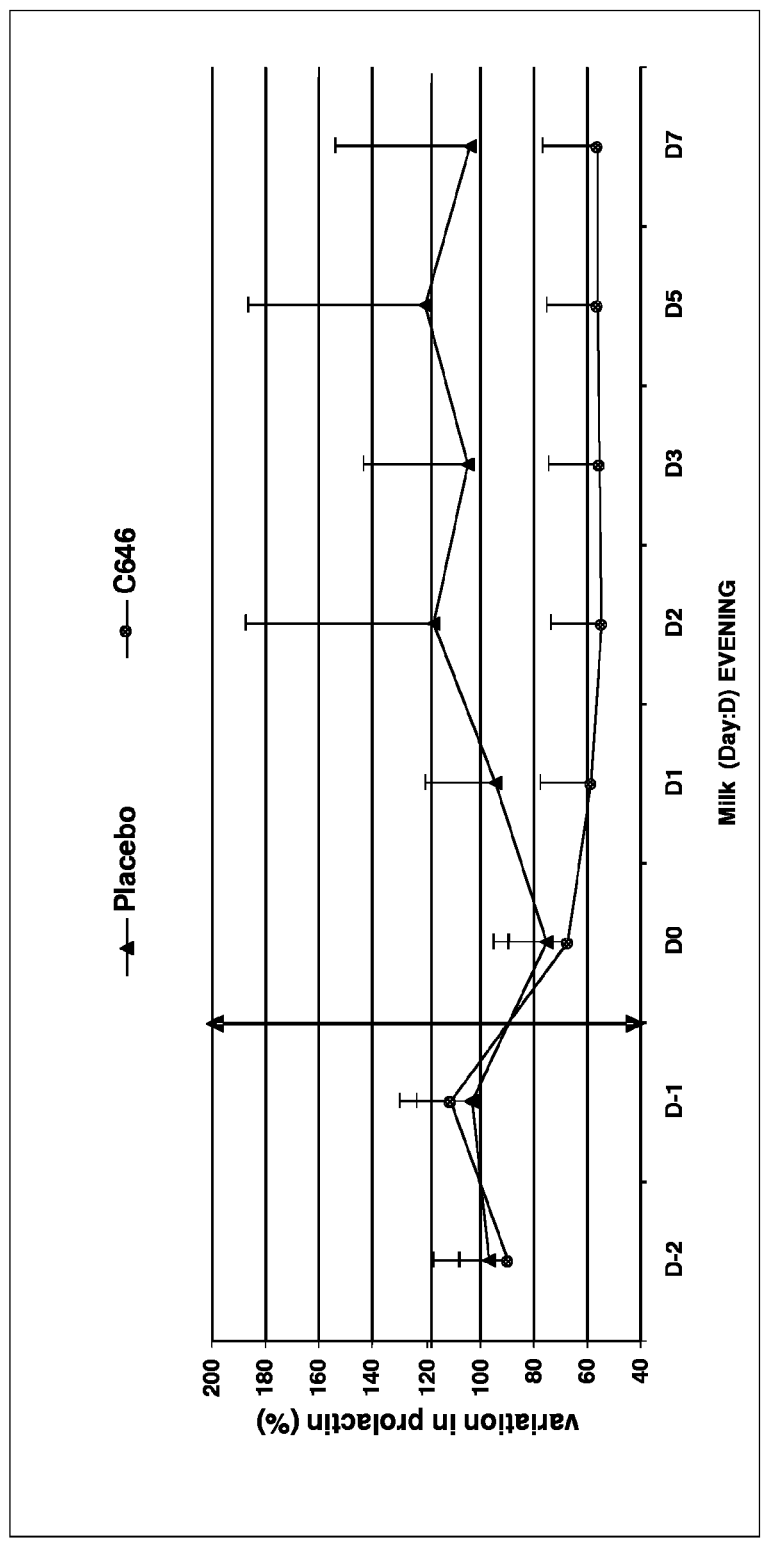
FIG. 2: is a graph that shows the variation in percentage of the prolactin rate observed every 24 hours during the period I (D-2 and D-1) and the period II (between D0 and D7), in comparison to a baseline of 100, following a single injection of 5 mcg/kg of Cabergoline on day D0, in a placebo group and in a group of treated animals (C646).

In parallel, the prolactin plasmatic concentrations decreased as shown in FIG. 2. The decrease in the plasmatic concentration in prolactin was very rapid, at 24 hrs following the injection, and was still present one week after the treatment. This prolactin decrease varies between 10 and 80% depending on the animals. The single administration of cabergoline demonstrated the correlation between the significant reduction of the milk production to the reduction of the plasmatic prolactin.

Example 3: Clinical Study of the Safety of Cabergoline-Based Veterinary Compositions in Ruminants This study aims to show the absence of risks such as abortions and fetus toxicity during the use of cabergoline in gestating ruminants even in the case of an overdose of cabergoline based veterinary compositions according to the regimen prescribed in the present invention. Groups of cows at different gestating stages receive the treatment at different doses:

- 3 months of gestation (6 animals), dose of 15 mcg/kg—2 injections at an interval of 48 hours
- 7 to 8 months of gestation: (5 animals), dose of 15 mcg/kg—2 injections at an interval of 48 hours
- 6.5 to 7.5 months of gestation: (11 animals), dose of 25 mcg/kg—2 injections an interval of 48 hours The formulation described in the Example 1, containing 500 mcg/ml of cabergoline in injectable solution is used in this study.

Regular clinical exams were conducted during a period lasting from 7 days before the treatment to 15 days after the treatment:

- Daily general inspection and abortions,
- Clinical exam of the genital tract including transrectal palpation and an ultrasound, in order to evaluate the suffering and fetal viability.

Blood samplings are conducted one day before the treatment and 15 days after the treatment to follow the plasmatic concentrations of different hormones and proteins indicating the health of the placenta and fetus, such as progesterone, estrone sulfate and the PAG (Pregnancy Associated Glycoprotein). The animals are followed until birth in order to evaluate the health of the newborn calves.

The results show that the two cabergoline injections at intervals of 48 hours to the dosage of 25 mcg/kg do not provoke any abortions; neither do they have any harmful effect on the gestation, or the viability and the health of the new born calves. No variation of the hormones indicating placental or fetal toxicity in connection with the treatments of different doses was observed.

In addition, animals generally tolerated the treatments well. In conclusion, a unique or repeated administration of cabergoline of duration of 48 hours of up to 25 mcg/kg is at least not risky in gestating cows.

Example 4: Clinical Study of the Efficiency and the Safety from Abortions of Quinagolide-Based Veterinary Compositions in Ruminants 9 multiparous cows of the Prim'Holstein race (approximately 600 kg) gestating for about approximately 7 months with a level of milk production of approximately 18 kg are included in this study. The study is organized as a <<cross-over>>: 2 treatments×2 periods, with a <<wash-out>> period of 3 weeks.

The animals receive the treatment Test via intramuscular injectable formulations.

Treatment Test: injectable solution of 0.5 mg/ml of quinagolide, 1 single intramuscular injection of a dose of 1 to 3 mg/per cow of 1 ml for 100 kg of body weight Treatment Control (Placebo): water for the injectable preparation, 1 single intramuscular injection of a volume identical to that of the treatment Test, i.e. 1 ml for 100 kg.

The follow up of the milk production is organized 7 days before and after the treatment day for each period, as well as the inspection of the abortions similar to Example 3 is conducted during the entire duration of the study.

Example 5: Clinical Study of the Efficiency and the Safety Against Abortions of the Bromocriptine Based Veterinary Solutions in Ruminants 9 multiparous cows of the Prim'Holstein race (approximately 600 kg) gestating for about 7 months with a level of milk production of about 18 kg are included in the study. The study is organized as a <<cross-over>>: 2 treatments×2 periods, with a <<wash-out>> period of 3 weeks.

The animals receive the treatment Test via intramuscular injectable formulations.

Treatment Test (bromocriptine): injectable solution of 10 mg/ml of bromocriptine, 1 single intramuscular injection of a dose of 100 to 200 mcg/kg that is 1 ml for 100 to 50 kg of corporal weight.

Treatment Control (Placebo): water for the injectable preparation, 1 single intramuscular injection of a volume that is identical to that of the treatment Test, i.e. 1 ml for 100 kg.

The follow up of the milk production is organized 7 days before and after the treatment day for each period, as well as the inspection of the abortions similar to Example 3 is conducted during the entire duration of the study.

The invention claimed is:

1. A method for treating or reducing the frequency of intra-mammary inflammations or infections of a gestating cow, and/or promoting mammary involution of a gestating cow, the method comprising the step of administrating to said gestating cow a veterinary composition comprising 500 mcg/ml cabergoline, wherein cabergoline is administered at a dose ranging from 5 µg/kg to 50 µg/kg, and wherein the veterinary composition is administered via a single intramuscular injection per treatment.

2. The method of claim 1, wherein said intra-mammary inflammations or infections is mastitis.

3. The method of claim 1, wherein cabergoline is administered at a dose ranging from 5 µg/kg to 25 µg/kg.

4. The method of claim 1, wherein cabergoline is administered at a dose of about 5 µg/kg.

* * * * *